(12) United States Patent
Imori et al.

(10) Patent No.: US 7,968,150 B2
(45) Date of Patent: Jun. 28, 2011

(54) METHOD OF SURFACE TREATMENT USING IMIDAZOLE COMPOUND

(75) Inventors: Toru Imori, Kitaibaraki (JP); Atsushi Yabe, Kitaibaraki (JP); Junnosuke Sekiguchi, Kitaibaraki (JP)

(73) Assignee: Nippon Mining & Metals Co., Ltd., Tokyo (JP)

( * ) Notice: Subject to any disclaimer, the term of this patent is extended or adjusted under 35 U.S.C. 154(b) by 246 days.

(21) Appl. No.: 12/290,328

(22) Filed: Oct. 29, 2008

(65) Prior Publication Data

US 2009/0068364 A1 Mar. 12, 2009

Related U.S. Application Data

(62) Division of application No. 10/515,708, filed as application No. PCT/JP03/09072 on Jul. 16, 2003, now abandoned.

(30) Foreign Application Priority Data

Jul. 29, 2002 (JP) .................................. 2002-219716

(51) Int. Cl.
*B05D 3/02* (2006.01)
*B32B 15/04* (2006.01)

(52) U.S. Cl. ........................................ 427/384; 428/457

(58) Field of Classification Search .................. None
See application file for complete search history.

(56) References Cited

U.S. PATENT DOCUMENTS

| 4,507,140 | A | 3/1985 | Sugavanam |
| 5,004,494 | A | 4/1991 | Sugavanam et al. |
| 5,698,391 | A | 12/1997 | Cook et al. |
| 5,886,177 | A | 3/1999 | Cook et al. |

FOREIGN PATENT DOCUMENTS

| JP | 60-181076 | 9/1985 |
| JP | 06-157471 | 6/1994 |
| WO | WO 95/18820 | 7/1995 |

*Primary Examiner* — San-Ming Hui
*Assistant Examiner* — Paul Zarek
(74) *Attorney, Agent, or Firm* — Flynn, Thiel, Boutell & Tanis, P.C.

(57) ABSTRACT

It is an object of the present invention to provide a novel imidazole alcohol compound that adheres strongly to metal surfaces in metal products, especially copper, aluminum and steel products, and that has a superior rust-preventive effect even in a thin film, and a surface-treating agent using the same. The novel imidazole alcohol compound is expressed by the following general formula (1) show a rust-preventive effect.

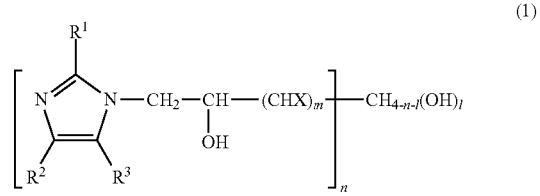

(In general formula (1), $R^1$, $R^2$ and $R^3$ are each hydrogen, a vinyl group or an alkyl group with 1 to 20 carbon atoms, an aromatic ring may be formed by $R^2$ and $R^3$, X indicates hydrogen, an alkyl group with 1 to 6 carbon atoms, or a substituent group which may contain N or O, m indicates an integer from 0 to 20, and n and l indicate integers from 1 to 3.) The above-mentioned imidazole alcohol compound can be produced by reacting an imidazole compound and an epoxy alcohol compound.

2 Claims, 3 Drawing Sheets

METHOD OF SURFACE TREATMENT USING IMIDAZOLE COMPOUND

CROSS-REFERENCE TO RELATED APPLICATION

This is a division of Ser. No. 10/515,708, filed Nov. 23, 2004, now abandoned which was the national stage of International Application No. PCT/JP03/09072, filed Jul. 16, 2003, which International Application was not published in English.

TECHNICAL FIELD

The present invention relates to novel imidazole alcohol compounds, a method for producing the same, and a surface-treating agent comprising the same as an active ingredient.

BACKGROUND ART

There are various requirements for the surfaces of various metal materials; rust-preventive properties may be cited as one important characteristic. Iron and steel products are used in various applications such as structures, automobiles, ships, cans and the like; in such applications, there are strong requirements for rust-preventive properties. Conventionally, various types of rust-preventive agents such as water-soluble rust-preventive agents, vaporizable rust-preventive agents, oil-based rust-preventive agents and the like have been used to obtain rust-preventive properties in iron and steel products. Generally, water-soluble rust-preventive agents are used for the purpose of temporary short-term rust prevention, and are not used for long-term rust prevention. Furthermore, vaporizable rust-preventive agents show an inherent rust-preventive power in a sealed state. Oil-based rust-preventive agents have a relatively strong rust-preventive power, and are able to provide long-term rust prevention; such agents include liquid-form rust-preventive oils, viscous rust-preventive greases, and agents in which rust-preventive additives, film forming additives or the like are dissolved in volatile organic solvents. However, rust-preventive oils and rust-preventive greases show stickiness following a surface treatment, and cannot be used as undercoating materials such as coating films or the like. Furthermore, agents formed by dissolving rust-preventive additives, film forming additives or the like in volatile organic solvents do no manifest a sufficient rust-preventive effect unless a thick film thickness is formed.

Moreover, zinc-plated steel plates are commercially marketed for the purpose of suppressing rust on iron. However, such plates prevent the rust of iron by means of a sacrificial anti-corrosion effect of zinc, which has a greater tendency toward ionization than iron. In this case, white rust of the zinc layer is prevented by further subjecting the surface of the zinc plating layer to a chemical conversion treatment such as a chromate treatment or the like, so that the rust-preventive properties are greatly reinforced. However, although such a chromate treatment produces a high rust-preventive effect even in a thin coating film, there is a demand for a rust-preventive coating film to replace this chromate treatment because of environmental problems. Currently, tannic acid has been proposed as a rust-preventive agent for zinc-plated steel plates; at present, however, it cannot be said that this has a sufficient effect compared to a chromate treatment.

Aluminum or aluminum alloys are light in weight, and have therefore attracted attention in various fields. However, since an aluminum oxide coating film is formed on the surface, the adhesion is not sufficient even in cases where the aluminum is directly coated with a paint. Numerous methods have been proposed as chemical conversion treatment methods for paint primary coating or undercoating, and numerous patent applications have currently been filed. At the present time, however, chromate treatment methods constitute the mainstream in the United States and Japan. However, as in the case of the above-mentioned zinc-plated steel plates, chromate treatments are undesirable from the standpoint of the environment, and there is a demand for a non-chromate treatment. Moreover, methods in which a treatment is performed with an alkali metal salt aqueous solution of silicic acid for the purpose of endowing the metal surface with characteristics such as corrosion resistance, static resistance and the like have also been proposed. In such methods, however, the treatment temperature is high, an immersion in boiling water or an immersion in an acid is performed as an after-treatment, and the desired characteristics cannot be obtained unless the alkali metal is removed.

DISCLOSURE OF THE INVENTION

It is an object of the present invention to provide novel imidazole alcohol compounds that can meet such requirements, i.e., that adhere strongly to metal surfaces in metal products, especially copper, aluminum and iron and steel products, and that have a superior rust-preventive effect even in a thin film, and a surface-treating agent using the same.

As a result of diligent research, the present inventors discovered that novel imidazole alcohol compounds expressed by the following general formula (1) have a superior rust-preventive effect on metal surfaces.

The present invention was devised on the basis of such a finding; the gist of this invention is as shown in (1) through (3) below.

(1) A novel imidazole alcohol compound expressed by the following general formula (1).

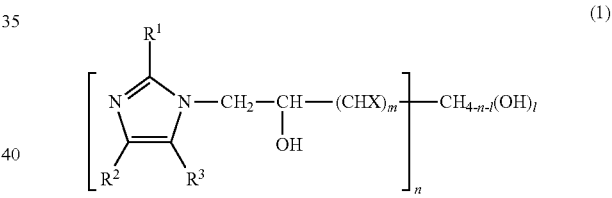

(In general formula (1), $R^1$, $R^2$ and $R^3$ are each hydrogen, a vinyl group or an alkyl group with 1 to 20 carbon atoms, an aromatic ring may be formed by $R^2$ and $R^3$, X indicates hydrogen, an alkyl group with 1 to 6 carbon atoms, or a substituent group which may contain N or O, m indicates an integer from 0 to 20, and n and l indicate integers from 1 to 3.)

(2) A process for producing the imidazole alcohol compound according to the above-mentioned (1), characterized by reacting an imidazole compound expressed by the following general formula (2) and an epoxy alcohol compound expressed by the following general formula (3).

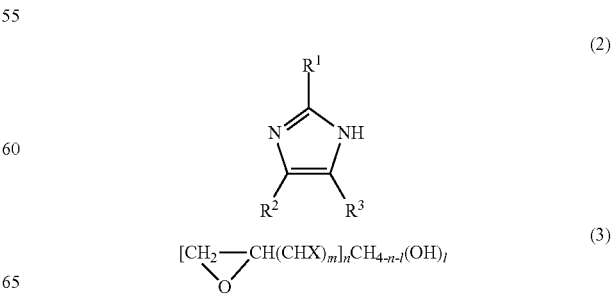

(In general formula (2), $R^1$, $R^2$ and $R^3$ are each hydrogen, a vinyl group or an alkyl group with 1 to 20 carbon atoms, and an aromatic ring may be formed by $R^2$ and $R^3$, and in general formula (3), X indicates hydrogen, an alkyl group with 1 to 6 carbon atoms, or a substituent group which may contain N or O, m indicates an integer from 0 to 20, and n and l indicate an integer from 1 to 3.)

(3) A surface-treating agent comprising the imidazole alcohol compound according to the above-mentioned (1) as an active ingredient.

The present invention will be described in greater detail below.

The effect of the present invention is sufficiently manifested if $R^1$, $R^2$ and $R^3$ in the above-mentioned general formulae (1) through (3) indicate hydrogen, vinyl groups or alkyl groups with 1 to 20 carbon atoms. Alkyl groups with 1 to 20 carbon atoms are desirable as alkyl groups. Furthermore, in cases where an aromatic ring is formed by $R^2$ and $R^3$, it is desirable that the aromatic ring that is formed be a benzene ring. X indicates hydrogen, an alkyl group with 1 to 6 carbon atoms, or a substituent group that may contain N or O. An alkyl group with 1 to 4 carbon atoms is desirable as the alkyl group with 1 to 6 carbon atoms, and hydroxy groups, carboxyl groups, amino groups and the like may be cited as examples of substituent groups that contain N or O.

The above-mentioned imidazole alcohol compounds (I) of the present invention are synthesized by the reaction expressed by the following reaction formula (4). Specifically, these compounds can be produced by mixing an imidazole compound and an epoxy alcohol compound, and heating this mixture to a temperature of 80 to 200° C.

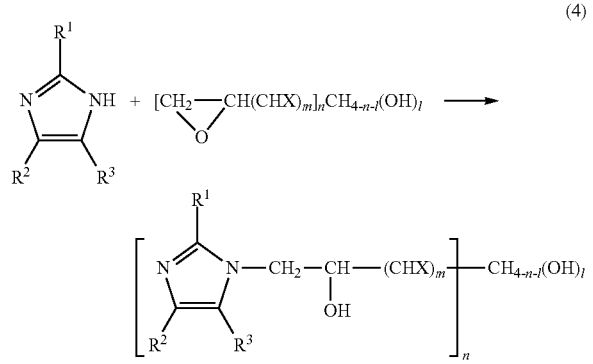

(4)

(In the above formula, $R^1$, $R^2$, $R^3$, X, l, m and n have the same definitions as described above.

Examples of desirable imidazole compounds expressed by the above-mentioned general formula (2) include imidazole, 2-alkylimidazoles, 2,4-dialkylimidazoles, 4-vinylimidazoles and the like. Especially desirable among these are imidazole; 2-methylimidazole, 2-ethylimidazole and 2-undecylimidazole as 2-alkylimidizoles; and 2-ethyl-4-methylimidazole and the like as 2,4-dialkylimidazoles.

Desirable examples of epoxy alcohol compounds expressed by the above-mentioned general formula (3) include epoxypropanol, epoxybutanol, epoxypentanol, epoxyhexanol and the like, and epoxypropanol is especially desirable.

It is advisable that the reaction of the above-mentioned imidazole compound and epoxy alcohol compound be performed by adding the epoxy alcohol compound dropwise to the imidazole compound heated to a temperature of 80 to 200° C. wherein the amount of the epoxy alcohol compound added is 0.1 to 10 times by mole as much as that of the imidazole compound. A reaction time of approximately 5 minutes to 2 hours is sufficient. This reaction does not always need a solvent; however, an organic solvent such as chloroform, dioxane, methanol, ethanol or the like may be used as a reaction solvent. Furthermore, since this reaction is averse to moisture, it is desirable to perform the reaction in a gas atmosphere that contains no moisture such as dried nitrogen, argon or the like, in order to prevent the inclusion of moisture.

The compounds of the present invention expressed by the above-mentioned general formula (1) can also be used as chemical mechanical polishing additives or wetting working agents; however, these compounds are especially useful as rust-preventive agents. When the imidazole alcohol compounds of the present invention are used on metals as surface-treating agents, it is generally desirable that these compounds be used in a form in which the compounds are diluted in a solvent. In this case, solvent-soluble resins (epoxy resins, acrylic resins or the like), silane coupling agents, viscosity adjusting agents, defoaming agents, ultraviolet absorbing agents, preservatives, surfactants and the like may also be added.

Solvents used in cases where the imidazole alcohol compounds of the present invention are used as surface-treating agents may be either aqueous type solvents or solvent type solvents. Examples of solvent type solvents include methanol, ethanol, isopropanol, toluene, ethyl acetate and the like.

The surface-treating agent of the present invention is used on metals; this agent has an especially superior rust-preventive effect on copper and copper alloys. Universally known coating methods such as spray coating, dip coating, brush coating and the like can be employed as the coating method used to apply the surface-treating agent of the present invention to a metal surface.

In order to obtain the effect of the surface-treating agent of the present invention to a sufficient extent, it is desirable that the agent be dried by heating following application as a coating. In this drying by heating, it is desirable that the coating be dried for 30 seconds to 60 minutes at 100 to 230° C. Under heating conditions following coating, the adsorption to the metal is heightened by the removal of moisture, so that the rust-preventive effect is enhanced. It is desirable that the thickness of the coating film following drying be 0.01 to 100 µm. A thickness of 0.05 to 10 µm is even more desirable. If the thickness is less than 0.01 µm, sufficient rust-preventive properties cannot be imparted, and if the thickness exceeds 100 µm, a uniform coating film cannot be obtained.

BEST MODE FOR CARRYING OUT THE INVENTION

The present invention will be concretely described below in terms of examples.

Example 1

Figure 1:
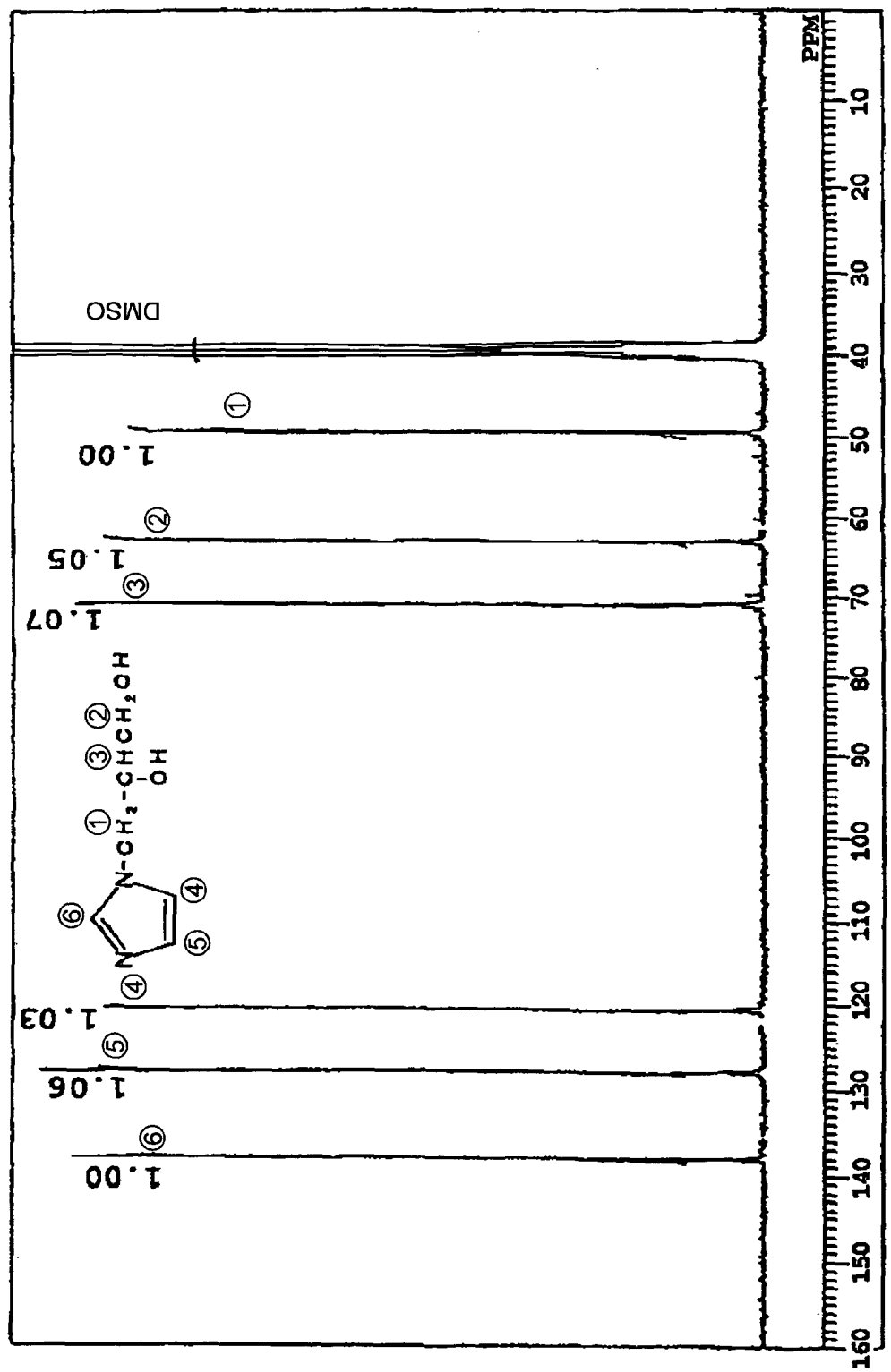
FIG. 1 shows the $^1$H-NMR spectrum of the novel imidazole alcohol compound of the present invention obtained in Example 1.

Synthesis of Imidazole Alcohol Compound 9.2 g of imidazole was heated to 120° C., and 10 g of 2,3-epoxypropanol was added to this dropwise. Afterward, a reaction was performed for 3 hours at 150° C., thus producing 19 g of the target product indicated by the following formula (5). The compound thus obtained was identified by NMR measurement. The $^1$H-NMR spectrum of this compound is shown in FIG. 1.

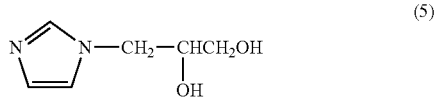
(5)

Example 2

Use as Surface-Treating Agent

Figure 2:
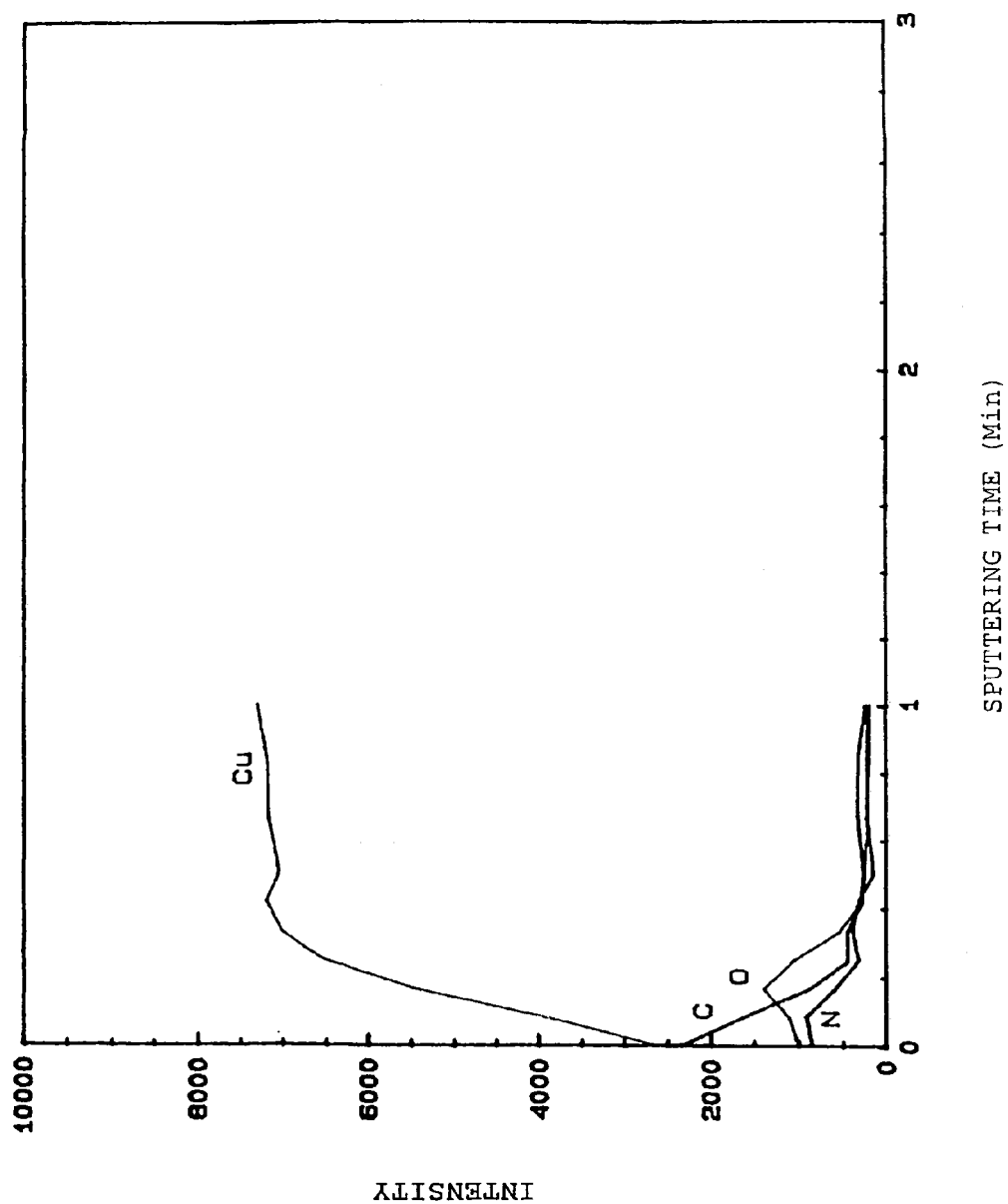
FIG. 2 shows the results of Auger analysis for Example 2.

A 10% aqueous solution (pH 11.6) of the imidazole alcohol compound (5) obtained in Example 1 was applied as a coating to the surface of a copper foil, and was heat-treated for 30 minutes at 150° C. Subsequently, Auger analysis was performed at an etching rate of 100 angstroms/min (calculated as SiO$_2$). The results are shown in FIG. 2. It is seen from FIG. 2 that a high rust-preventive effect was manifested at a high pH with little oxygen detected.

Comparative Example 1

Figure 3:
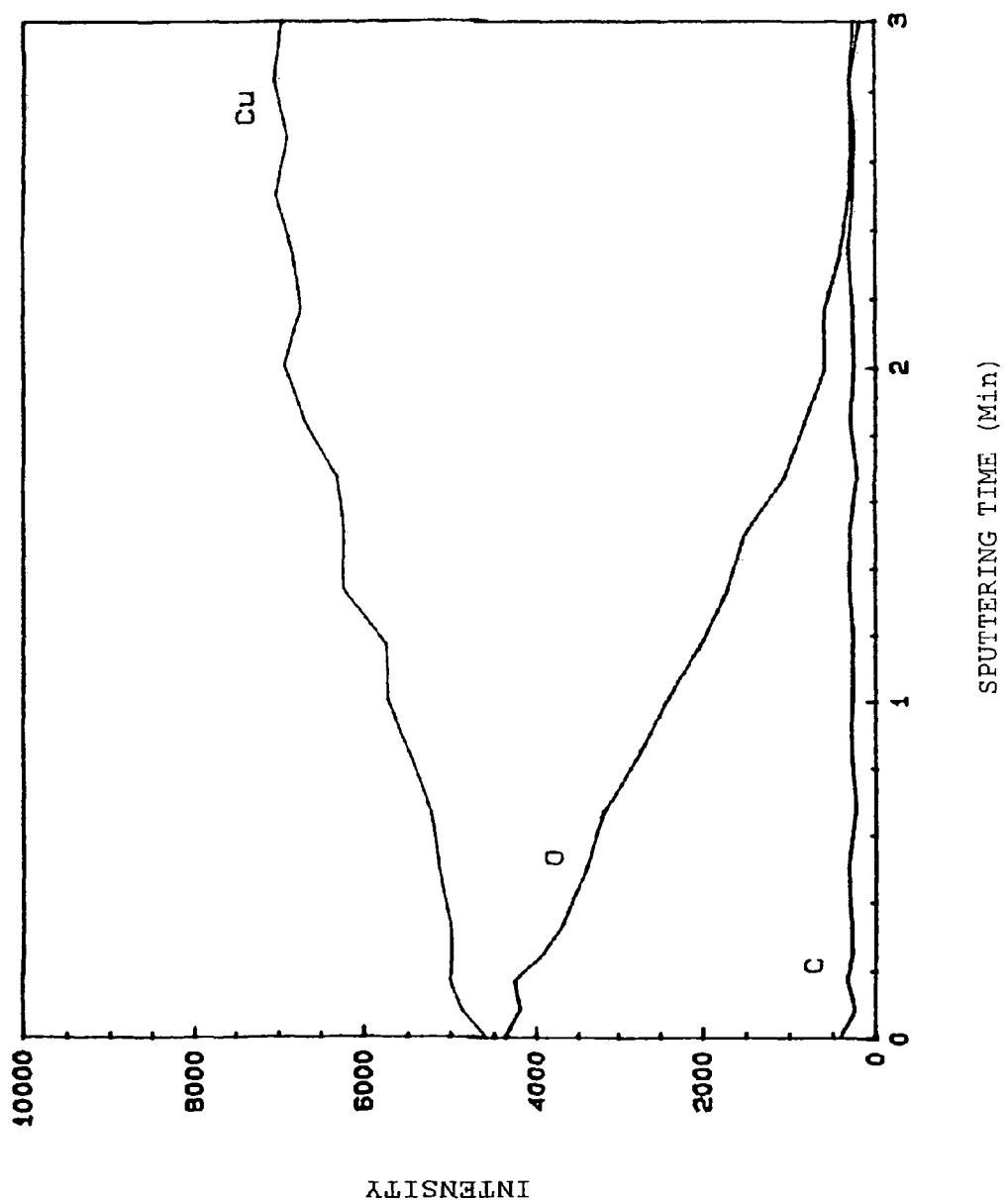
FIG. 3 shows the results of Auger analysis for Example 1.

An experiment similar to the examples was performed, except that the copper foil was not coated with the compound of the present invention. Auger analysis was performed in the same manner. The results are shown in FIG. 3.

INDUSTRIAL APPLICABILITY

Compositions containing the imidazole alcohol compounds of the present invention show superior rust-preventive properties.

What is claimed is:

1. A method of surface-treating a metal comprising applying to the surface of the metal a surface-treating agent comprising, as an active ingredient, an imidazole expressed by the following general formula (1)

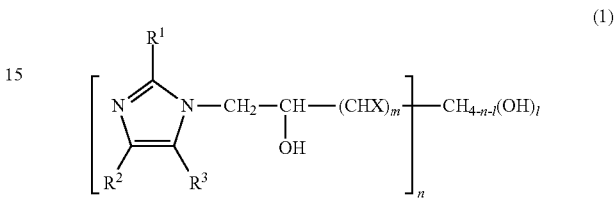
(1)

wherein in general formula (1), R$^1$, R$^2$ and R$^3$ are each hydrogen, a vinyl group or an alkyl group with 1 to 20 carbon atoms, an aromatic ring may be formed by R$^2$ and R$^3$, X indicates hydrogen, an alkyl group with 1 to 6 carbon atoms, m indicates an integer from 0 to 20, and n and l indicate integers from 1 to 3 and n+l does not exceed 4.

2. The method of claim 1, additionally comprising the step of drying the surface of the metal after the surface-treating agent has been applied thereto at a temperature of 100 to 230° C. for a time period of from 30 to 60 minutes.

* * * * *